(12) United States Patent
Yan

(10) Patent No.: US 10,568,543 B2
(45) Date of Patent: Feb. 25, 2020

(54) METHOD AND APPARATUS FOR TESTING VITAL CAPACITY

(71) Applicant: Goertek Inc., Weifang (CN)

(72) Inventor: Wenming Yan, Weifang (CN)

(73) Assignee: Goertek Inc., Weifang (CN)

(*) Notice: Subject to any disclaimer, the term of this patent is extended or adjusted under 35 U.S.C. 154(b) by 408 days.

(21) Appl. No.: 15/507,612

(22) PCT Filed: Jun. 29, 2015

(86) PCT No.: PCT/CN2015/082671
§ 371 (c)(1),
(2) Date: Feb. 28, 2017

(87) PCT Pub. No.: WO2016/090899
PCT Pub. Date: Jun. 16, 2016

(65) Prior Publication Data
US 2017/0281052 A1  Oct. 5, 2017

(30) Foreign Application Priority Data
Dec. 12, 2014  (CN) .......................... 2014 1 0772806

(51) Int. Cl.
*A61B 5/091*  (2006.01)
*A61B 5/00*  (2006.01)
(Continued)

(52) U.S. Cl.
CPC .............. *A61B 5/091* (2013.01); *A61B 5/085* (2013.01); *A61B 5/087* (2013.01); *A61B 5/097* (2013.01); *A61B 5/113* (2013.01); *A61B 5/6898* (2013.01)

(58) Field of Classification Search
CPC ......... A61B 5/085; A61B 5/087; A61B 5/091; A61B 5/097; A61B 5/113
See application file for complete search history.

(56) References Cited

U.S. PATENT DOCUMENTS

| 4,844,085 A | 7/1989 | Gattinoni |
| 5,137,026 A | 8/1992 | Waterson et al. |

(Continued)

FOREIGN PATENT DOCUMENTS

| CA | 2872785 A1 | 11/2013 |
| CN | 2367251 Y | 3/2000 |

(Continued)

OTHER PUBLICATIONS

International Bureau of WIPO, International Search Report and Written Opinion in Application No. PCT/CN2015/082671, dated Oct. 9, 2015.

(Continued)

*Primary Examiner* — Daniel L Cerioni
*Assistant Examiner* — Raymond P Dulman
(74) *Attorney, Agent, or Firm* — LKGlobal | Lorenz & Kopf, LLP

(57) ABSTRACT

The present application discloses a method and apparatus for testing vital capacity. The method comprises: measuring a static pressure $P_0$ of a pressure hole inner cavity of a mobile device; wherein the pressure hole is communication with the exterior and is purposely disposed on the mobile device or is an already-designed opening; obtaining an air pressure $P(t)$ at each moment by blowing air towards the pressure hole; obtaining an air flow speed $v(t)$ corresponding to each moment according to a correspondence relation formula between the air flow speed $v(t)$ and a pressure differential $P(t)-P_0$; and obtaining vital capacity Vc of the subject according to a correspondence relationship between a measurement time t and the air flow speed $v(t)$.

8 Claims, 2 Drawing Sheets

(51) Int. Cl.
    *A61B 5/087*    (2006.01)
    *A61B 5/113*    (2006.01)
    *A61B 5/085*    (2006.01)
    *A61B 5/097*    (2006.01)

(56) References Cited

U.S. PATENT DOCUMENTS

| | | | |
|---|---|---|---|
| 5,347,843 A | 9/1994 | Orr et al. | |
| 2003/0101827 A1* | 6/2003 | Cha | A61B 5/087 |
| | | | 73/861.66 |
| 2007/0239058 A1 | 10/2007 | Krasilchikov et al. | |
| 2009/0156952 A1* | 6/2009 | Hunter | A61M 16/024 |
| | | | 600/538 |
| 2010/0286548 A1* | 11/2010 | Lazar | A61B 5/087 |
| | | | 600/538 |
| 2011/0201958 A1* | 8/2011 | Lazar | A61B 5/097 |
| | | | 600/538 |
| 2017/0270260 A1* | 9/2017 | Shetty | A61B 5/6898 |

FOREIGN PATENT DOCUMENTS

| | | |
|---|---|---|
| CN | 201355840 Y | 12/2009 |
| CN | 102423262 A | 4/2012 |
| CN | 102497472 A | 6/2012 |
| CN | 103393416 A | 11/2013 |
| CN | 104586396 A | 5/2015 |
| WO | 2014037843 A1 | 3/2014 |

OTHER PUBLICATIONS

Chinese Patent Office, Examination Report in Application No. 201410772806.2 dated May 4, 2016.

\* cited by examiner

METHOD AND APPARATUS FOR TESTING VITAL CAPACITY

CROSS-REFERENCE TO RELATED APPLICATION

This application is a U.S. National-Stage entry under 35 U.S.C. § 371 based on International Application No. PCT/CN2015/082671, filed Jun. 29, 2015, which was published under PCT Article 21(2) and which claims priority to Chinese Application No. 201410772806.2, filed Dec. 12, 2014, which are all hereby incorporated herein in their entirety by reference.

TECHNICAL FIELD

This application pertains to the technical field of mobile terminals, and particularly to a method and apparatus for testing vital capacity.

BACKGROUND

Current mobile phones and wearable devices usually use a microphone as a testing sensor for testing vital capacity based on the principle of calculating an air flow speed by testing a vibration frequency of a diaphragm caused by air. Since the diaphragm of the microphone is thin and highly sensitive and apt to break under a high-frequency pressure and cause failure, the calculation precision is not high and the testing result is unreliable.

In addition, other objects, desirable features and characteristics will become apparent from the subsequent summary and detailed description, and the appended claims, taken in conjunction with the accompanying drawings and this background.

SUMMARY

The present application provides a method and apparatus for testing vital capacity to solve problems such as undesirable vital capacity measurement precision of microphones and likelihood of damages to microphones in the prior art.

To achieve the above object, the technical solution of the present application is implemented as follows:

According to an aspect of the present application, the present application provides a method for testing vital capacity, comprising:

measuring a static pressure $P_0$ of a pressure hole inner cavity of a mobile device; wherein the pressure hole is communicated with the exterior and is purposely disposed on the mobile device or is an already-designed opening;

obtaining an air pressure $P(t)$ at each moment by blowing air towards the pressure hole;

obtaining an air flow speed $v(t)$ corresponding to each moment according to a correspondence relation formula between the air flow speed $v(t)$ and a pressure differential $P(t)-P_0$; and obtaining vital capacity Vc of the subject according to a correspondence relationship between a measurement time t and the air flow speed $v(t)$.

Preferably, the obtaining an air flow speed $v(t)$ corresponding to each moment according to a correspondence relation formula between the air flow speed $v(t)$ and a pressure differential $P(t)-P_0$ comprises:

obtaining the air flow speed $v(t)$ at the current moment according to a formula $$v(t) = \sqrt{\frac{2(P(t)-P_0)}{\rho}},$$

wherein $\rho$ is air density.

Preferably, the obtaining vital capacity Vc of the subject according to a correspondence relationship between a measurement time t and the air flow speed $v(t)$ comprises:

obtaining the vital capacity Vc of the subject according to a formula $$Vc = s\int_0^t t \cdot v(t) dt,$$

wherein s is a cross section of the pressure hole inner cavity.

Preferably, the obtaining vital capacity Vc of the subject according to a correspondence relationship between a measurement time t and the air flow speed $v(t)$ comprises:

obtaining the vital capacity Vc of the subject according to a formula $$Vc = t \cdot s \sqrt{\frac{2(P_{max}-P_0)}{\rho}},$$

wherein $P_{max}$ is a maximum air pressure value obtained within the measurement time t, and s is a cross section of the pressure hole inner cavity.

Preferably, the mobile device comprises a mobile phone or a wearable device.

According to another aspect of the present application, an embodiment of the present application provides a testing apparatus for vital capacity, comprising:

a pressure sensor disposed in a pressure hole inner cavity of the testing apparatus, wherein the pressure hole is communicated with the exterior and is purposely disposed on the testing apparatus or is an already-designed opening, and configured to obtain an air pressure $P(t)$ at each moment by blowing air towards the pressure hole; and a vital capacity obtaining unit configured to obtain an air flow speed $v(t)$ corresponding to each moment according to a correspondence relation formula between the air flow $v(t)$ speed and a pressure differential $P(t)-P_0$, and obtain vital capacity Vc of the subject according to a correspondence relationship between a measurement time t and the air flow speed $v(t)$.

Preferably, the vital capacity obtaining unit comprises: an air flow speed obtaining module configured to obtain the air flow speed $v(t)$ at the current moment according to a formula $$v(t) = \sqrt{\frac{2(P(t)-P_0)}{\rho}},$$

wherein $\rho$ is air density.

Preferably, the vital capacity obtaining unit is specifically used to obtain the vital capacity Vc of the subject according to a formula $$Vc = s\int_0^t tgv(t)dt,$$

wherein s is a cross section of the pressure hole inner cavity.

Preferably, the vital capacity obtaining unit is specifically used to obtain the vital capacity Vc of the subject according to a formula $$Vc = t \cdot s \sqrt{\frac{2(P_{max} - P_0)}{\rho}},$$

wherein $P_{max}$ is a maximum air pressure value obtained within the measurement time t, and s is a cross section of the pressure hole inner cavity.

Preferably, the testing apparatus for vital capacity is disposed in a mobile device, and the mobile device comprises a mobile phone or a wearable device.

The advantageous effects of the embodiments of the present application are as follows: the embodiments of the present application disclose a method and apparatus for testing vital capacity. The method by using the pressure sensor obtains a static pressure in the inner cavity of the testing apparatus and obtains an air pressure at each moment by blowing air towards the pressure hole, and obtains an air flow speed corresponding to each moment according to a correspondence relationship between the air flow speed and a pressure differential between the air pressure and static pressure at each moment; and obtains the vital capacity of the subject according to the correspondence relationship between the air flow speed and the measurement time. The technical solution may effectively improve the vital capacity measurement precision, does not cause damages to related components of the mobile device, and is completely different from the method of using a microphone to measure vital capacity in the prior art.

BRIEF DESCRIPTION OF THE DRAWINGS

The present invention will hereinafter be described in conjunction with the following drawing figures, wherein like numerals denote like elements, and.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description.

Embodiments of the present application will be described below in further detail in conjunction with figures to make the objectives, technical solutions and advantages of the present application clearer.

Figure 1:
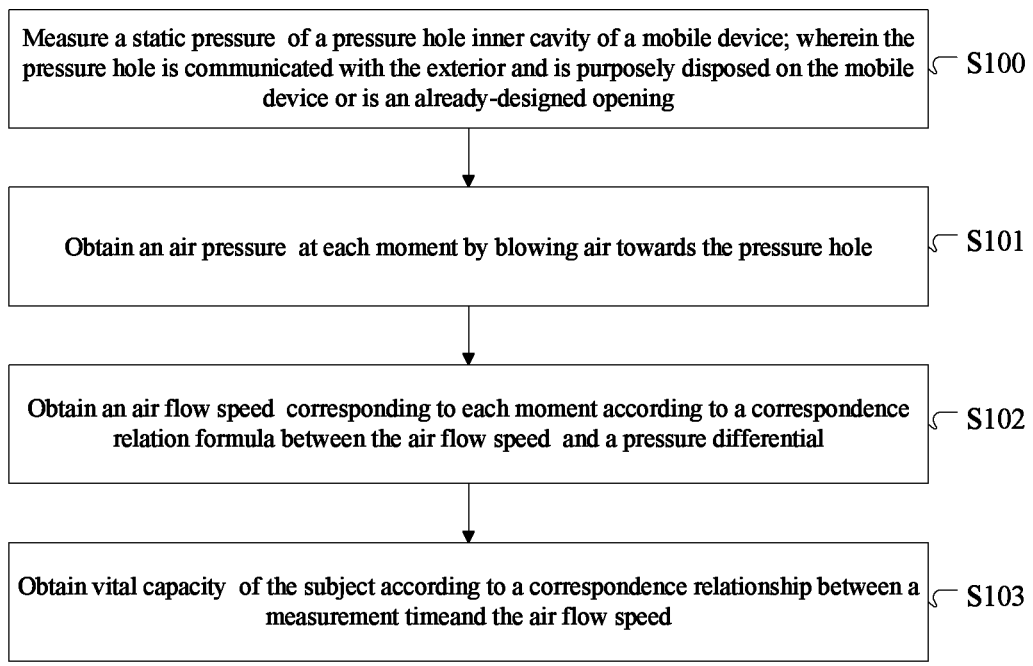
FIG. 1 is a flow chart of a method for testing vital capacity according to an embodiment of the present application.
Figure 3:
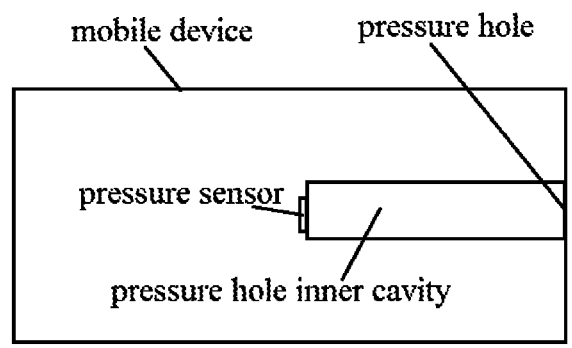
FIG. 3 is a structural schematic view of a mobile device according to an embodiment of the present application.

FIG. 1 is a flow chart of a method for testing vital capacity according to an embodiment of the present application. FIG. 3 is a structural schematic view of a mobile device according to an embodiment of the present disclosure. The method comprises:

S100: measuring a static pressure $P_0$ of a pressure hole inner cavity of a mobile device; wherein the pressure hole is communicated with the exterior and is purposely disposed on the mobile device or is an already-designed opening.

In that, the mobile device may be a mobile phone, a wearable device or the like.

Since an excessive cross section of the pressure hole inner cavity affects the air flow speed and further affects the vital capacity measurement precision, in practical application the inner diameter of the pressure hole inner cavity is generally set to be about 3.5 mm, but not limited to that, and the cross section of its inner cavity may be set specifically according to the design structure and the application needs of the mobile device.

Noticeably, the pressure hole may be arranged purposely in cooperation with the design structure of the mobile device, or other openings of the mobile device itself, such as the earphone jack, the power supply hole or other openings for connection with the exterior may be used as the pressure hole in the present embodiment to make the appearance of the mobile device simple and pleasant.

S101: blowing air towards the pressure hole and obtaining an air pressure P(t) at each moment.

S102: obtaining an air flow speed v(t) corresponding to each moment according to a correspondence relation formula between the air flow speed v(t) and a pressure differential $P(t)-P_0$.

Specifically, the air flow speed v(t) at the current moment is obtained according to a formula $$v(t) = \sqrt{\frac{2(P(t) - P_0)}{\rho}},$$

wherein ρ is air density.

It is appreciated that the air density ρ in the present embodiment may be the air density constant 1.205 kg/m³ at a normal temperature and under a normal pressure, or the density of air exhaled by a subject may be obtained by other methods.

S103: obtaining vital capacity Vc of the subject according to a correspondence relationship between a measurement time t and the air flow speed v(t).

In a preferred embodiment, the method obtains the vital capacity Vc of the subject by the following method:

obtaining the vital capacity Vc of the subject according to an integral formula $$Vc = s\int_0^t tgv(t)dt,$$

wherein s is a cross section of the pressure hole inner cavity.

The vital capacity of the subject within the measurement time can be obtained accurately by the method according to the preferred embodiment.

In another preferred embodiment, the method obtains the vital capacity Vc of the subject by the following method:

obtaining the vital capacity Vc of the subject according to a maximum value formula $$Vc = tgs\sqrt{\frac{2(P_{max} - P_0)}{\rho}},$$

wherein $P_{max}$ is a maximum air pressure value obtained within the measurement time t, and s is a cross section of the pressure hole inner cavity.

The method according to the preferred embodiment is relatively simple and can quickly obtain the vital capacity of the subject within the measurement time. In practical application, the vital capacity may be calculated by selecting a proper calculation formula according to needs.

Figure 2:
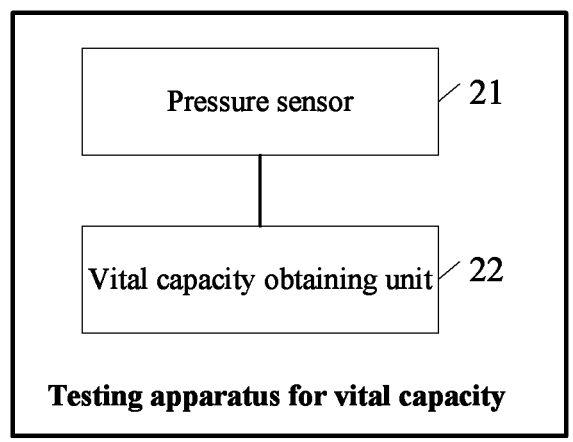
FIG. 2 is a structural schematic view of a testing apparatus for vital capacity according to an embodiment of the present application.

FIG. 2 is a structural schematic view of a testing apparatus for vital capacity according to an embodiment of the present application. The testing apparatus for vital capacity comprises:

a pressure sensor 21 disposed in a pressure hole inner cavity of the testing apparatus, wherein the pressure hole is communicated with the exterior and is purposely disposed on the testing apparatus or is an already-designed opening, and configured to obtain an air pressure P(t) at each moment by blowing air towards the pressure hole; and a vital capacity obtaining unit 22 configured to obtain an air flow speed v(t) corresponding to each moment according to a correspondence relation formula between the air flow speed v(t) and a pressure differential P(t)–$P_0$, and obtain vital capacity Vc of the subject according to a correspondence relationship between a measurement time t and the air flow speed v(t).

The testing apparatus for vital capacity in the present embodiment may be disposed in a mobile device such as a mobile phone or a wearable device.

Preferably, the vital capacity obtaining unit 22 comprises:

an air flow speed obtaining module configured to obtain the air flow speed v(t) at the current moment according to a formula $$v(t) = \sqrt{\frac{2(P(t) - P_0)}{\rho}},$$

wherein $\rho$ is air density.

In a preferred embodiment, the vital capacity obtaining unit 22 obtains the vital capacity Vc of the subject according to an integral formula $$Vc = s\int_0^t tgv(t)dt,$$

wherein s is a cross section of the pressure hole inner cavity.

In another preferred embodiment, the vital capacity obtaining unit 22 obtains the vital capacity Vc of the subject according to a maximum value formula $$Vc = tgs\sqrt{\frac{2(P_{max} - P_0)}{\rho}},$$

wherein $P_{max}$ is a maximum air pressure value obtained within the measurement time t, and s is a cross section of the pressure hole inner cavity.

In the above two preferred embodiments, two different calculation formulas are used to obtain the vital capacity of the subject: the integral formula can achieve a more accurate measurement result, whereas the maximum value formula is simple and can quickly obtain the measurement result. In practical application, the vital capacity may be calculated by selecting a proper calculation formula according to needs.

To conclude, the embodiments of the present application disclose a method and apparatus for testing vital capacity. The method by using the pressure sensor obtains a static pressure in the inner cavity of the testing apparatus and obtains an air pressure at each moment by blowing air towards the pressure hole, and obtains the air flow speed corresponding to each moment according to a correspondence relationship between the air flow speed and a pressure differential between the air pressure and static pressure at each moment; and obtains the vital capacity of the subject according to the correspondence relationship between the air flow speed and the measurement time. The technical solution may effectively improve the vital capacity measurement precision, does not cause damages to related components of the mobile device, and is completely different from the method of using a microphone to measure vital capacity in the prior art.

What are described above are only preferred embodiments of the present application and not intended to limit the protection scope of the present application. Any modifications, equivalent substitutions and improvements made within the spirit and principle of the present application are all included in the protection scope of the present application.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the invention as set forth in the appended claims and their legal equivalents.

The invention claimed is:

1. A method for testing vital capacity, wherein the method comprises:

measuring a static pressure $P_0$ of a pressure hole inner cavity of a mobile device; wherein the pressure hole is communicated with an exterior and is purposely disposed on the mobile device or is an already-designed opening;

obtaining an air pressure P(t) at each moment by blowing air towards the pressure hole;

obtaining an air flow speed v(t) corresponding to each moment according to a correspondence relation formula between the air flow speed v(t) and a pressure differential P(t)–$P_0$; and obtaining vital capacity Vc of the subject according to a correspondence relationship between a measurement time t and the air flow speed v(t);

wherein the mobile device comprises a mobile phone or a wearable device.

2. The method for testing vital capacity according to claim 1, wherein, the obtaining an air flow speed v(t) corresponding to each moment according to a correspondence relation formula between the air flow speed v(t) and a pressure differential $P(t)-P_0$ comprises:

obtaining the air flow speed v(t) at the current moment according to a formula $$v(t) = \sqrt{\frac{2(P(t) - P_0)}{\rho}},$$

wherein $\rho$ is air density.

3. The method for testing vital capacity according to claim 1, wherein, the obtaining vital capacity Vc of the subject according to a correspondence relationship between a measurement time t and the air flow speed v(t) comprises:

obtaining the vital capacity Vc of the subject according to a formula $$Vc = s \int_0^t t \cdot v(t) dt,$$

wherein s is a cross section of the pressure hole inner cavity.

4. The method for testing vital capacity according to claim 1, wherein the obtaining the vital capacity Vc of the subject according to a correspondence relationship between a measurement time t and the air flow speed v(t) comprises:

obtaining the vital capacity Vc of the subject according to a formula $$Vc = t \cdot s \sqrt{\frac{2(P_{max} - P_0)}{\rho}},$$

wherein $\rho$ is air density, $P_{max}$ is a maximum air pressure value obtained within the measurement time t, and s is a cross section of the pressure hole inner cavity.

5. A testing apparatus for vital capacity, wherein the apparatus comprises:

a pressure sensor disposed in a pressure hole inner cavity of the testing apparatus, wherein the pressure hole is communicated with an exterior and is purposely disposed on the testing apparatus or is an already-designed opening, and configured to obtain an air pressure P(t) at each moment by blowing air towards the pressure hole; and a vital capacity obtaining unit configured to obtain an air flow speed v(t) corresponding to each moment according to a correspondence relation formula between the air flow speed v(t) and a pressure differential $P(t)-P_0$, and obtain vital capacity Vc of the subject according to a correspondence relationship between a measurement time t and the air flow speed v(t), wherein $P_0$ is a static pressure of the pressure hole inner cavity of the testing apparatus;

wherein the testing apparatus for vital capacity is disposed in a mobile device, and the mobile device comprises a mobile phone or a wearable device.

6. The testing apparatus for vital capacity according to claim 5, wherein the vital capacity obtaining unit comprises:

an air flow speed obtaining module configured to obtain the air flow speed v(t) at the current moment according to a formula $$v(t) = \sqrt{\frac{2(P(t) - P_0)}{\rho}},$$

wherein $\rho$ is air density.

7. The testing apparatus for vital capacity according to claim 5, wherein the vital capacity obtaining unit is specifically used to, obtain the vital capacity Vc of the subject according to a formula $$Vc = s \int_0^t t \cdot v(t) dt,$$

wherein s is a cross section of the pressure hole inner cavity.

8. The testing apparatus for vital capacity according to claim 5, wherein the vital capacity obtaining unit is specifically used to, obtain the vital capacity Vc of the subject according to a formula $$Vc = t \cdot s \sqrt{\frac{2(P_{max} - P_0)}{\rho}},$$

wherein $\rho$ is air density, $P_{max}$ is a maximum air pressure value obtained within the measurement time t, and s is a cross section of the pressure hole inner cavity.

* * * * *